United States Patent [19]

Petisce

[11] Patent Number: 5,037,763
[45] Date of Patent: Aug. 6, 1991

[54] ARTICLE COATED WITH CURED MATERIAL AND METHODS OF MAKING

[75] Inventor: James R. Petisce, Norcross, Ga.

[73] Assignee: AT&T Bell Laboratories, Murray Hill, N.J.

[21] Appl. No.: 579,220

[22] Filed: Sep. 5, 1990

Related U.S. Application Data

[63] Continuation of Ser. No. 330,658, Mar. 30, 1989, abandoned.

[51] Int. Cl.[5] .............................................. G01N 21/64
[52] U.S. Cl. ...................................... 436/172; 436/85; 436/56; 436/34; 250/302; 250/459.1; 356/317; 356/318; 356/417; 427/8; 73/150 R; 264/40.1; 264/40.2; 264/21
[58] Field of Search ............................ 250/302, 459.1; 356/317, 318, 417; 427/8; 73/150 R; 264/40.1, 40.2, 21; 436/85, 56, 34, 172

[56] References Cited

U.S. PATENT DOCUMENTS

| | | | |
|---|---|---|---|
| 4,444,701 | 4/1984 | Meguiar | 264/40.1 |
| 4,474,830 | 10/1984 | Taylor | 427/54.1 |
| 4,547,040 | 10/1985 | Yamamoto et al. | 350/96.3 |
| 4,548,771 | 10/1985 | Senapati et al. | 264/25 |
| 4,639,080 | 1/1987 | Kimura et al. | 350/96.34 |
| 4,651,011 | 3/1987 | Ors et al. | 250/459.1 |
| 4,702,867 | 10/1987 | Sejimo et al. | 264/25 |
| 4,740,055 | 4/1988 | Kanda et al. | 350/96.3 |
| 4,798,346 | 1/1989 | Myers et al. | 242/18 A |

OTHER PUBLICATIONS

Wang et al., *Polymer*, 1986, vol. 27, Oct., pp. 1529–1532.
Wang et al., *Photophysics of Polymers*, Chapter 33, 1987, pp. 454–462.
Application Ser. No. 07/213,875 filed on Jun. 30, 1988 in the names of K. W. Jackson, et al.
Chemical Abstracts vol. 107, No. 18 Nov. 1987, p. 372, abstract No. 160094q.
Chemical Abstracts vol. 109, No. 12, Sep. 19, 1988, p. 34, abstract No. 94125p.

*Primary Examiner*—Jack I. Berman
*Attorney, Agent, or Firm*—E. W. Somrs

[57] ABSTRACT

An article such as a drawn optical fiber (21) or an array of optical fibers is provided with a curable coating material. The array of optical fibers may be held together with a curable matrix material (45). Included in the coating material or the matrix material is a fluorescent constituent the fluorescence emission of which changes as a function of the degree of cure of the coating or matrix material. After the in-line curing of the coating material or of the matrix material, the fluorescence emission of the fluorescent constituent is monitored to determine the degree of cure of the curable material.

12 Claims, 5 Drawing Sheets

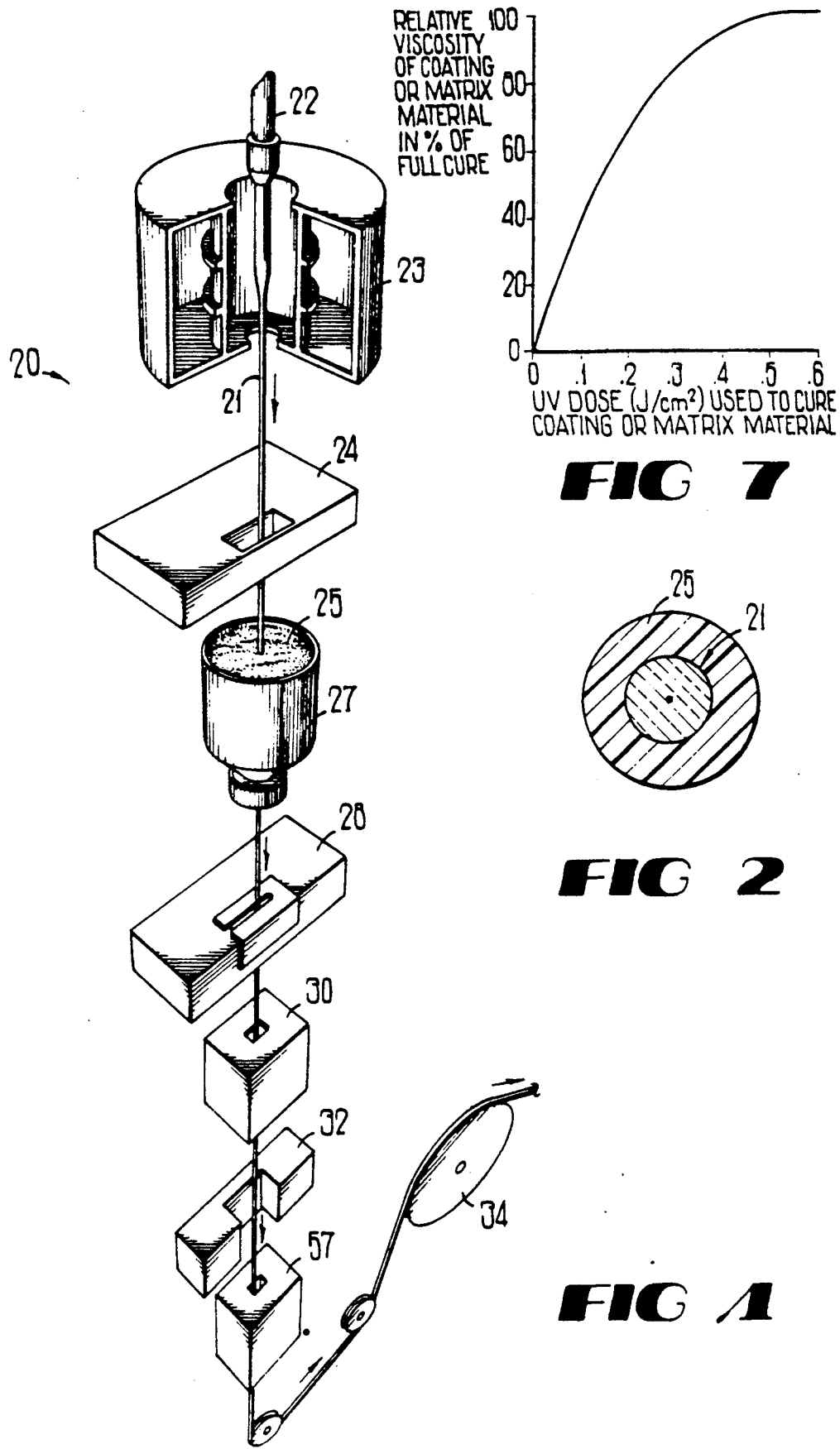

ARTICLE COATED WITH CURED MATERIAL AND METHODS OF MAKING

This application is a continuation of application Ser. No. 07/330,658, filed on 3/30/89, now abandoned.

TECHNICAL FIELD

This invention relates to an article coated with a cured material and to methods of making. More particularly, it relates to methods of providing optical fiber or fibers with a curable coating or matrix material and for monitoring in-line the degree of cure of such materials.

BACKGROUND OF THE INVENTION

After only a somewhat recent introduction, optical fiber has had a meteoric rise as the predominant means of transmission media in voice and data communications. Optical fiber is manufactured by drawing the fiber from a preform which is made by any of several well known processes. Afterwards, or as part of a tandem process, the drawn fiber is coated, cured, measured and taken up, desirably in an automatic takeup apparatus, on a spool. Methods and apparatus for taking up optical fiber are disclosed and claimed in U.S. Pat. No. 4,798,346 which issued on Jan. 17, 1989 in the names of D. L. Myers and J. G. Wright. Typically, an optical fiber has a diameter on the order of 125 microns, for example, and is covered with a coating material which increases the outer diameter of the coated fiber to about 250 microns, for example.

The optical fibers thus produced may be assembled into units and provided with a sheathing system. Or a plurality of optical fibers may be assembled into a planar array and secured in place by a curable matrix material such as is disclosed in application Ser. No. 213,876 which was filed on June 30, 1988 in the names of K. W. Jackson, et al, now U.S. Pat. No. 4,900,126. This last described product is referred to as a bonded ribbon.

In both the process for coating the optical fiber after it is drawn, which may include the application of primary and secondary curable coating materials, and in the process for embedding an array of optical fibers in a cured matrix material, it becomes important to be able to determine the degree of cure of the curable coating or matrix material.

Suitable curing of the optical fiber coating and of the ribbon matrix material is very important. An improperly cured bonded ribbon matrix or optical fiber coating material will inhibit cabling. Also an undercured coating or matrix material generally will emit an undesirable odor. Further, improperly cured coating and matrix materials exhibit poor strippability, poor adhesion and poor reliability relative to a properly cured coating and matrix material. As should be evident, properly cured coating and matrix materials for drawn optical fibers and for optical fiber ribbons are important to the quality of the final product. Further, the modulus of the cured of material is a function of the degree of cure. Modulus is important to the mechanical and optical performance of the optical fiber and fiber ribbon.

Presently, there are several methods which are used to determine the degree of cure of optical fiber coating materials. In one method, which is referred to as in-situ modulus test, a cut is made through the coating or coating layers to the glass. A load is applied to the optical fiber and measurements are taken as to the time during which the load is applied to the fiber and the distance through which the optical fiber moves. From these measurements, the modulus of the primary coating can be determined.

In a pull-out test, a length of optical fiber is positioned in a well known Instron apparatus. The force which is necessary to pull the optical fiber from the primary coating material is measured. This measurement is proportional to the degree of cure. In a third method which is referred to as the cut-through method, a length of coated optical fiber is placed into a fixture which prevents rolling of the fiber. A knife probe is caused to engage the fiber and that temperature at which the knife edge probe penetrates the coating material is measured. The greater the measured temperature, the greater the degree of cure.

There are several problems with respect to the use of the foregoing methods. First, each requires the use of relatively expensive equipment. Secondly, each is a so-called off-line test and hence is most likely not performed on 100 percent of the product throughput. Thirdly, a high level of employee training is required and lastly, the tests are operator sensitive.

Needless to say, it is most desirable that in-line testing for the degree of cure be accomplished as the optical fiber or optical fiber ribbon is being moved along a path of travel to a takeup. Bonded ribbon production line speeds may be in the range of about 200 feet per minute. If an off-line test were used to determine the degree of cure and hence the modulus, and if that test were to consume about five minutes, then it can be seen that about 12000 feet of optical fiber, assuming a twelve fiber ribbon, may be wasted if the degree of cure is not sufficient.

The problem of determining the degree of cure of a curable coating material exists in industries other than that for optical fiber manufacture. For example, curable materials are used in the manufacture of floor tiles, furniture, medical syringes, compact discs, computer floppy discs, video and audio tapes and glass fiber composites for automobiles and other products.

What is needed and what is not provided by the prior art are methods of monitoring the degree of cure of curable coating materials. What is especially sought after are methods of determining the degree of cure of curable coating and matrix materials which are used to provide optical fiber transmission media. Desirably, the sought after products and methods and apparatus for making same should be capable of being performed as the optical fiber or as the optical fiber ribbon is being moved along a manufacturing line.

SUMMARY OF THE INVENTION

The foregoing problems of the prior art have been overcome with the article of this invention which may be an elongated strand material and with the methods for making same. The article comprises a substrate material and a material system which encloses at least partially the substrate material. The material system comprises a curable material. Also included in the material system is a probe comprising a material which emits light subsequent to being promoted to an exicted electronic state. The material system is such that its emission of light changes as a function of the degree of cure of the curable material. The article may be, for example, an optical fiber or an optical fiber array which is enclosed in a curable coating or matrix material. Preferably, the probe and curable coating or matrix material comprise a material system, the fluorescence emission of which changes as a function of the degree of cure of the coating or matrix material.

In the manufacture of optical fiber, for example, optical fiber is advanced along a path of travel and a curable coating material is applied thereto. The coating material which is applied to the optical fiber includes a fluorescent constituent which is such that its fluorescence emission changes as a function of the degree of cure of the coating material. Then the coating material is cured and, in-line, the fluorescence emission of the fluorescent constituent is monitored to determine the degree of cure of the coating material. The optical fiber having the cured coating material is taken up. Instead of an optical fiber, the methods of this invention may be used to determine the degree of cure of a matrix material which is used to hold together a plurality of optical fibers which are disposed in a planar array. In either case, the in-line monitoring allows steps to be taken to adjust the degree of cure to that value desired.

An apparatus for making an optical fiber which includes a curable coating material or bonded optical fiber ribbon which includes a curable matrix material includes a manufacturing line for advancing an optical fiber coated with a UV curable material or a plurality of optical fibers which have been gathered together and embedded in a UV curable matrix material past a source of UV radiation energy. Afterwards, the coated optical fiber or the bonded ribbon is advanced past a detector which is effective to measure the degree of cure. As should be realized, the degree of cure is related to the modulus of the coating or of the matrix material. Should the degree of cure and hence the modulus not be as desired, the detector may be used to alert an operator who makes appropriate changes to obtain the desired degree of cure. The coated optical fiber or the bonded ribbon is then taken up on a spool.

BRIEF DESCRIPTION OF THE DRAWING

Other features of the present invention will be more readily understood from the following detailed description of specific embodiments thereof when read in conjunction with the accompanying drawings, in which:

FIG. 1 is a schematic view of a manufacturing line which is used to provide one or multiple coating materials for a drawn optical fiber;

FIG. 2 is an end view in section of an optical fiber having a coating provided by portions of the apparatus of FIG. 1;

FIG. 7 is a graph which depicts the relationship of viscosity of a curable coating or matrix material to a UV dose which is used to cure the coating or matrix material;

FIG. 11 is a graph which shows absorption spectra for a coating or matrix material and for a probe and an emission spectrum for the probe;

DETAILED DESCRIPTION

Figure 3:
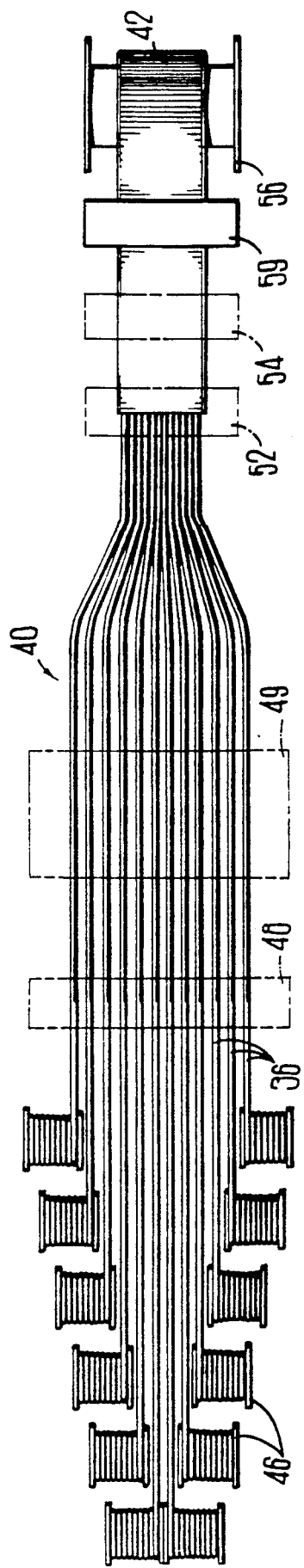
FIG. 3 is a schematic view of a manufacturing line which is used to provide a matrix material for a plurality of optical fibers disposed in an array.

Referring now to FIG. 1, there is shown an apparatus which is designated generally by the numeral 20 and which is used to draw optical fiber 21 from a specially prepared cylindrical preform 22 and for then coating the fiber. The optical fiber 21 is formed by locally and symmetrically heating the preform 22, typically 7 to 25 mm in diameter and 60 cm in length, to a temperature of about 2000° C. As the preform is fed into and through a furnace 23, fiber 21 is drawn from the molten material.

As can be seen in FIG. 1, the elements of the draw system include the furnace 23 wherein the preform is drawn down to the fiber size after which the fiber 21 is pulled from the heat zone. The diameter of the fiber 21 is measured by a device 24 at a point shortly after the fiber is formed and this measured value becomes an input into a control system. Within the control system, the measured diameter is compared to the desired value and an output signal is generated to adjust the draw speed such that the fiber diameter approaches the desired value.

After the diameter of the fiber 21 is measured, a protective coating 25 (see also FIG. 2) is applied to it by apparatus 27. Preservation of fiber strength requires the application of the protective coating, which shields newly drawn fiber from the deleterious effects of the atmosphere. This coating must be applied in a manner that does not damage the surface of the fiber 21 and such that the fiber has a predetermined diameter and is protected from abrasion during subsequent manufacturing operations, installation and service. Minimizing attenuation requires the selection of a suitable coating material and a controlled application of it to the fiber. Such a coating apparatus may be one such as that described in U.S. Pat. No. 4,474,830 which issued on Oct. 2, 1984 in the name of C. R. Taylor. Minimizing diameter variation which in turn minimizes the losses due to misalignment at connector and splice points requires careful design of the draw system and the continuous monitoring and control of the fiber diameter during the drawing and the coating steps of the process. Then, the coated fiber 21 is passed through a centering gauge 28.

After the coating material has been applied to the drawn fiber, the coating material must be cured. Accordingly, the optical fiber having the coating material thereon is passed through a device 30 for curing the coating and a device 32 for measuring the outer diameter of the coated fiber. Afterwards, it is moved through a capstan 34 and is spooled for testing and storage prior to subsequent cable operations.

Referring now to FIG. 3, there is shown a schematic view of a manufacturing line which is designated generally the numeral 40. The line 40 is capable of manufacturing a bonded ribbon 42 (see FIG. 4). The ribbon 42 includes a plurality of coated optical fibers 36–36 each of which includes a core, a cladding and one or more layers 25–25 of coating material.

Figure 4:
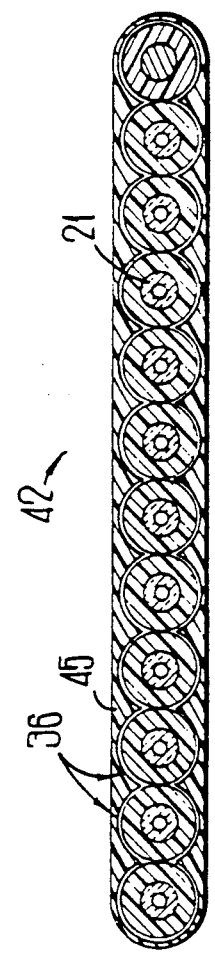
FIG. 4 is an end view in section of an optical fiber array which is embedded in a matrix material.

As can be seen in FIG. 4, the optical fibers 36–36 may be disposed in a planar array. The fibers are held bonded together in that array by a matrix material 45. It is common to refer to such a structure as a bonded ribbon. In a preferred embodiment, the matrix material is an ultraviolet (UV) curable material.

Along the line 40, a plurality of the optical fibers 36–36 are payed out from supplies 46–46, and an ink from a reservoir is applied thereto by an applicator 48. Afterwards, the ink is dried in an oven 49. Then the optical fibers are gathered together and embedded in the curable matrix material in an applicator 52. The applicator 52 may be an extruder, for example. Afterwards, the array in the matrix material is directed past an apparatus 54 which is well known and which is used to cure the curable matrix material and taken up on a spool 56.

Figure 5:
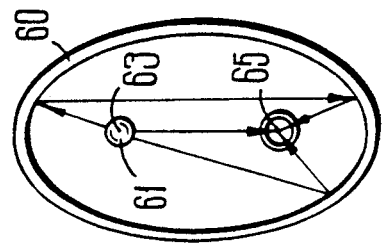
FIG. 5 is a cross sectional view an elliptical reflector which is used to cure the optical fiber coating or matrix materials.

As mentioned, after the curable coating material has been applied to the drawn optical fiber or the curable matrix material to the array of optical fibers, the coating or the matrix material must be cured. The coating material may be cured by thermal, electron beam, microwave or ultrasonic energy or as in the preferred embodiment with ultraviolet energy. For the preferred embodiment, the curable material may comprise a silicone-based material, an acrylate-based material, a methacrylate-based material, a polyimide-based material or a vinyl-based material. The curing of the bonded ribbon, for example, may be accomplished within apparatus which includes an elliptical reflector 60 (see FIG. 5). In it a lamp 61 is positioned at one of two focal points 63 and 65 and the article at the other. The lamp 61 is such that it emits energy at wavelengths which are suitable to cure the curable material.

Figure 6:
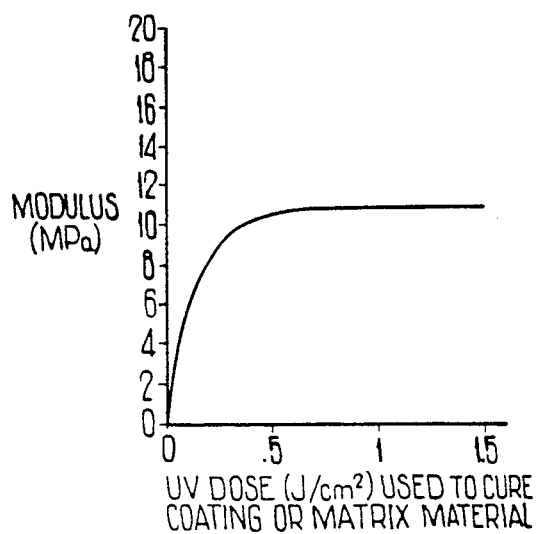
FIG. 6 depicts the modulus of a curable coating or matrix material as plotted against radiation cure dose.

The modulus of the cured coating material is dependent on the U.V. curing dose (see FIG. 6). In order to cause the modulus of the coating material or the matrix material 45 of the bonded ribbon to be a desired value, the degree of cure is monitored. Although reference hereinafter may be made only to the coating material or to the matrix material, it should be understood that the following applies to both. The methods of this invention facilitate the in-line monitoring of the degree of cure. This is accomplished by including a probe in the coating material or in the matrix material. The probe comprises a material which emits light subsequent to being promoted to an excited electronic state.

In the apparatus 20, an in-line cure detector system 57 is included after the curing apparatus 30 whereas in the apparatus 40, an in-line detector system 59 precedes the spool 56. Broadly, the in-line cure detector system includes a light source which emits appropriate wavelengths necessary to promote the probe to an excited electronic state and a detector which is capable of quantitatively measuring the intensity of emission from the probe as it transitions from the excited electronic state to an unexcited electronic state.

The curable matrix material, for example, is a material system which comprises a composition comprising an ultraviolet (UV) curable material such as an acrylate and a probe such as, for example, a fluorescent constituent. Hereinafter, the description is couched in terms of a UV curable coating or matrix material and a fluorescent probe. The system is such that its emission of light changes as a function of the degree of cure of the curable material. Emission from the fluorescent material provides a signature or a fingerprint of the probe constituent in the material. This signature or fingerprint remains with the curable material after the curable material has been cured and provides about the same emission level thereafter.

The unique excitation and emission spectra of a material system functions as the signature or fingerprint for the curable material system or for the final product subsequent to manufacture. After the UV absorption spectrum of the material system or of the article containing the cured system has been determined, excitation at the longest wavelength of the UV absorption spectrum will yield a fluorescence emission spectrum. Subsequently, determination of the characteristic fluorescence excitation spectrum for the wavelength corresponding to the maximum fluorescence emission will yield the excitation spectrum of the fluorescent probe. The very fact that an emission spectrum results upon excitation of the curable material system or of the article containing the cured material system is indicative of the use of a curable material system which includes a constituent probe.

The enclosing material system of the optical fiber or of the fiber array must be one such that under cure, the fluorescence emission of the material system changes with the degree of cure. The fluorescent probe constituent is such that its fluorescence emission is dependent on the degree of cure of the coating or matrix material.

Properties of the fluorescent material may change because of the change in the polymer coating material which changes the fluorescence emission of the probe. There are several ways in which the fluorescence emission may change and these are best seen by relating that change to viscosity of the coating or matrix material being cured.

The probe is an organic material that has a fluorescent form that may be dependent on its orientation in space. That orientation is dependent on its mobility which changes with the degree of cure of the optical fiber coating or matrix material. As the coating or matrix material cures, its viscosity increases (see FIG. 7) until it becomes a solid. At that time, there is no further increase in viscosity and further change in fluorescence emission does not occur.

Figure 8:
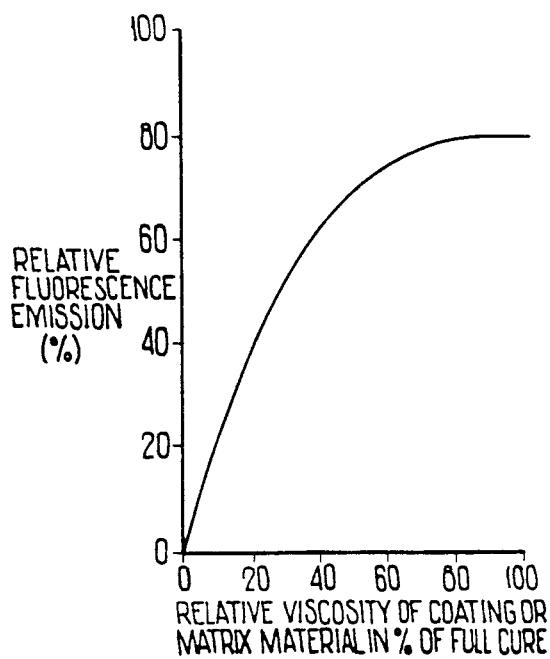
FIGS. 8, 9 and 10 are graphs which show relative fluorescence emission of fluorescent materials versus relative viscosity of coating or matrix material in percent of full cure.
Figure 9:
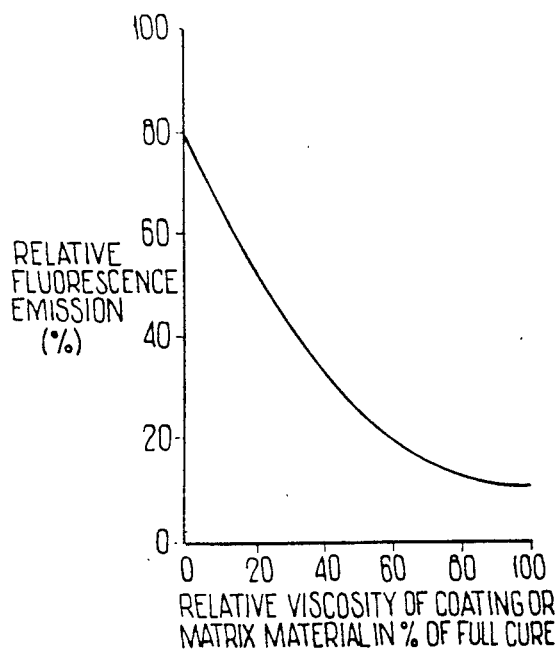

For those probe materials in which the fluorescence emission is dependent on orientation in space, the emission may increase as a function of viscosity (see FIG. 8) or it may decrease (see FIG. 9). Further, the curable coating or matrix system may include a fluorescent constituent which is such that it is independent of the viscosity (see FIG. 10), however, in that type the fluorescence emission of the system is such that it changes as a function of the absorption of the coating or matrix material which is dependent on the degree of cure of the coating or matrix material.

If as the enclosing coating or matrix material is cured and its viscosity increases, the orientation of the probe favors increased fluorescence, then the intensity of emission increases as a function of the degree of cure (see again FIG. 8). During cure of the optical fiber coating or matrix material, the motion of the fluorescent probe is restricted to favor the fluorescent form. A system which includes a coating or matrix material and this kind of probe may be referred to as a Type A system. On the other hand, if as the enclosing coating or matrix material is cured and viscosity increases, the orientation favors less fluorescence, then the intensity of emission decreases as a function of cure (see again FIG. 9). A system which includes a coating or a matrix material and this latter kind of probe is referred to herein as a Type B system.

For the foregoing two approaches, i.e. types A and B, the absorption wavelength of the fluorescent probe must exceed substantially that of the matrix material. Any overlap of the absorption of the coating or matrix material with the absorption of the probe must be insubstantial. Viewing now FIG. 11, there is shown a graph which depicts absorption of the coating or matrix material and of the probe and fluorescence emission of the probe plotted as a function of wavelength. As can be seen, the wavelength at which the fluorescence emission of the probe is a maximum is displaced from that at which the absorption of the probe reaches a maximum value. This displacement of the emission wavelength from the absorption wavelength is well known and is referred to as the Stokes shift. If this condition be satisfied as in FIG. 11, then any change in the probe emission is due to a change of its orientation in space and hence of its fluorescence as a function of the degree of cure. This arrangement is effective because as the coating or matrix material transitions from a liquid to a solid material, its viscosity increases from about 10000 cps at 23° C. to a solid. The more viscous the matrix material, the less mobile is the probe material. As the degree of cure increases, the relative intensity of the emission of the probe increases or decreases, unaffected by the absorption or emission of the coating or of the matrix material.

Figure 10:
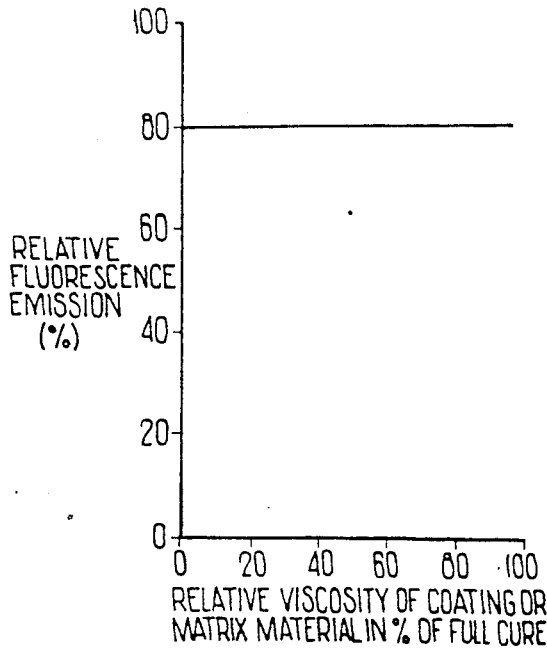

A third approach is to use a fluorescent probe constituent which is independent of the viscosity of the coating or matrix material during cure (see again FIG. 10). A system which includes a coating material and such a probe is referred to herein as a Type C system. Such a system is ideal when the absorption characteristic of the probe is substantially the same as that of the coating or matrix material. If the fluorescence of the probe remains the same as a function of the viscosity of the medium which is dependent on the degree of cure, then reliance must be put on the properties of the coating or matrix material. The transmission of the coating or matrix material changes as a function of the degree of cure.

Figure 12:
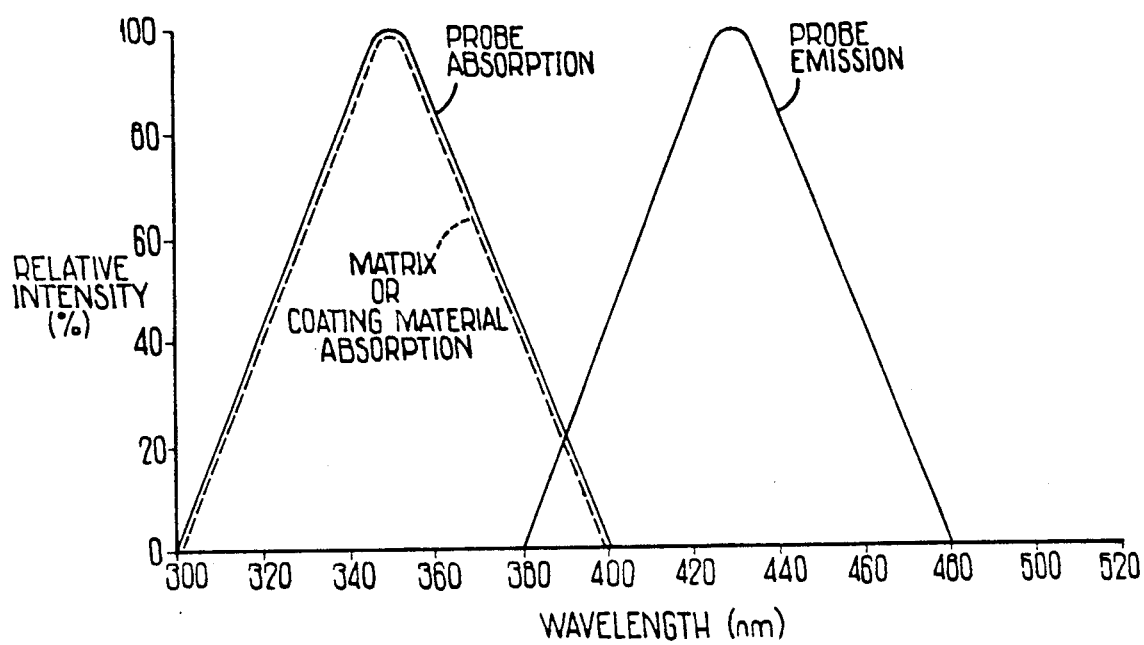
FIG. 12 is another graph which shows an absorption spectra for a coating or matrix material and for a probe and an emission spectrum for the probe.

For a Type C system to be a viable one, there are three requirements. First, it must be known that the emission intensity of the probe is not dependent on its orientation in space which is dependent on the viscosity of the coating or matrix material. That is, the fluorescence is independent of the viscosity of the medium. Secondly, it must be known that the excitation spectrum of the probe is coincident with or has somewhat substantial overlap with the absorption spectrum of the curable matrix or coating material (see FIG. 12). Thirdly, the coating or matrix material must have an absorption which is cure dependent.

Figure 14:
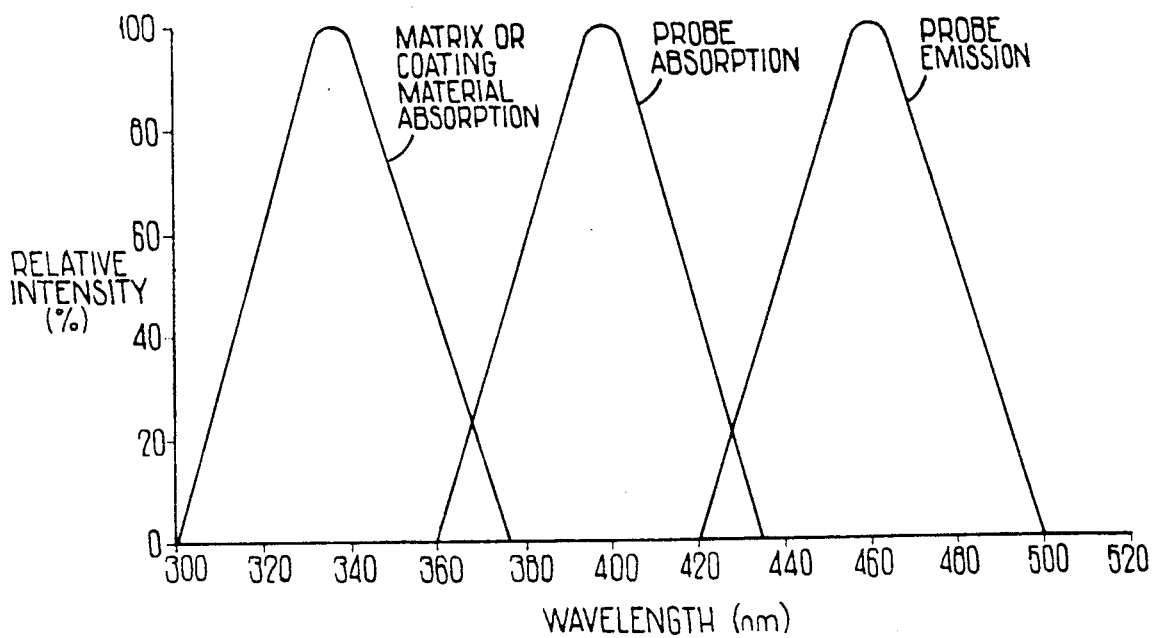
FIGS. 13 and 14 show, respectively, relative coating or matrix material absorption versus radiation dose, and relative absorption versus wavelength as a function of cure for a material the absorption of which increases as a function of the degree of cure.
Figure 13:
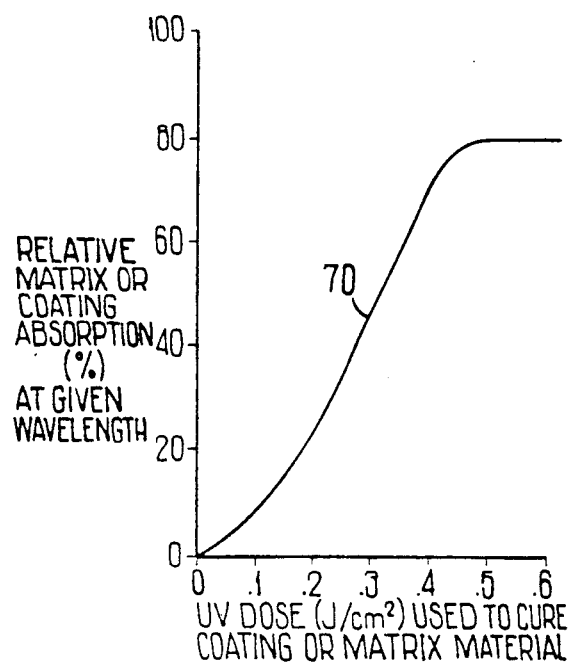
Figure 14:
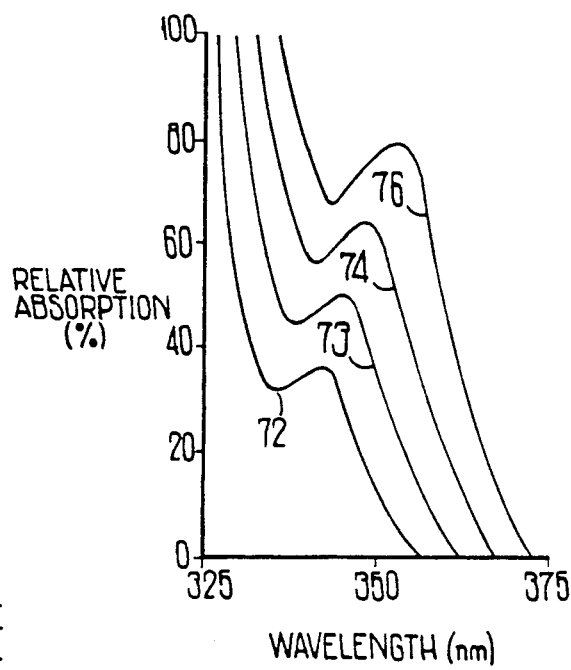

For some UV coating and matrix materials, percent relative absorption of UV radiation increases with respect to the radiation curing dose. For example, viewing FIG. 13, it is seen that a curve 70 increases until it plateaus at about 80% absorption at a given wavelength. Viewing now FIG. 14, there is shown a family of curves 72, 73, 74 and 76 with the relative absorption in percent being the ordinate and the wavelength of radiation being the abscissa. The curve 72 of FIG. 14 represents a coating or matrix material in liquid form. For curve 73, the cure dose is 0.13 Joule/cm$^2$, for curve 74, 0.25 Joule/cm$^2$ and for curve 76, 0.5 Joule/cm$^2$. These curves illustrate that for some materials, the UV absorption increases with the degree of cure.

Figure 15:
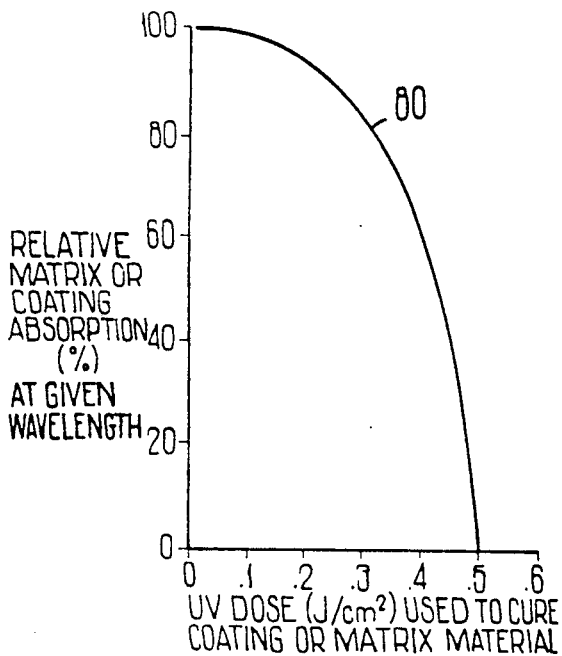
FIGS. 15 and 16 show, respectively, relative coating or matrix material absorption versus radiation dose, and relative absorption versus wavelength as a function of cure for a material the absorption of which decreases as a function of the degree of cure.
Figure 16:
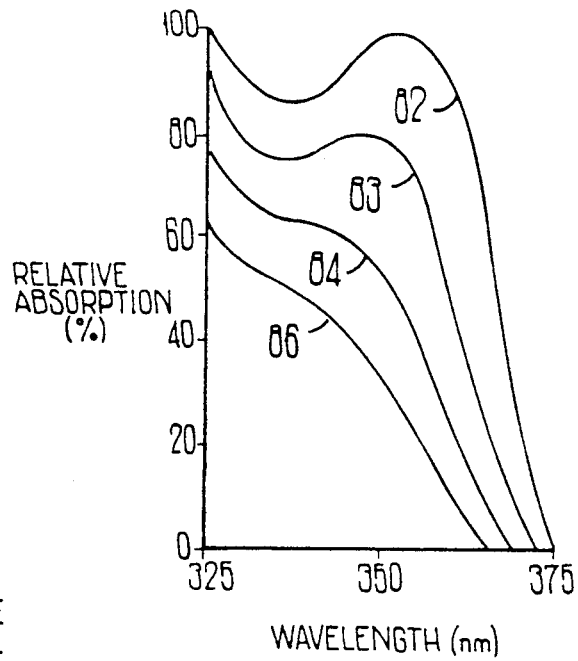

For other UV coating and matrix materials, the absorption decreases as a function of the degree of cure. Curves exemplary of these kinds of materials are shown in FIGS. 15 and 16. As is seen by a curve 80 in FIG. 15, the relative absorption in percent of a matrix or coating material decreases with increasing radiation curing dose as expressed in Joules per square centimeter. In FIG. 16, a family of curves 82, 83, 84 and 86 represent plots of the relative absorption in percent versus wavelength. The curve 82 represents a liquid as applied as a coating or as a matrix material. As is seen, as the coating or the matrix materials represented by this family of curves undergo an increasing cure dose of radiation energy, the percent absorption decreases. The curve 83 represents a plot of percent absorption versus wavelength for a cure dose of 0.13 Joule/cm$^2$, curve 84 for 0.25 Joule/cm$^2$ and curve 86 for 0.5 Joule/cm$^2$.

Transmission and absorption are inversely related. If the above-mentioned three requirements for a Type C system be met and a coating or matrix material as characterized by the graphs of FIGS. 13 and 14 be used, then upon excitation, as the matrix material absorbs more radiation as a function of cure, there is less light which reaches the probe constituent and hence there is less fluorescence emission. The greater the cure of the matrix material, the more its absorption increases. In effect, the arrangement uses the attenuation of light reaching the probe to excite it. Conversely, if a coating or matrix material characterized by the graphs of FIGS. 15 and 16 be used, then upon excitation, as the coating or matrix material absorbs less radiation as a function of cure, more light reaches the probe constituent and hence there is more fluorescence emission.

A Type C system is operative independent of the viscosity of the coating or matrix material whereas type A or B includes a viscosity dependent probe. Instead, in a Type C system, reliance is placed on the absorption of the coating or matrix material to attenuate the light which excites the probe. In using the probe characterized by FIG. 10, the fluorescence of the coating or matrix system does not depend on the mobility of the probe, but rather on the light absorption of the coating or matrix material. In this kind of coating system, the absorption of the coating or matrix material changes as it cures. This is not desirable in the types shown in FIGS. 8 and 9, for there, a fluorescent probe, the absorption of which is different from that of the matrix, is chosen.

In none of the three techniques described hereinabove does the fluorescent material cure. Rather it is trapped in the matrix or in the optical fiber coating material. In Type A and B systems, the probe mobility becomes restricted as the viscosity of the coating or matrix material increases and the fluorescence changes. In a Type C system, reliance is placed on the absorption of the coating or matrix material because the probe has a fluorescence emission which is viscosity independent. Further, the fluorescence emission of the material system is substantially constant over time, and, following cure of the curable coating or matrix material, functions as a fingerprint for the system at anytime thereafter.

There are other kinds of probes which may be used. If a probe is consumed by, for example, a photoreaction, less absorption may occur. One of these other kinds of probes is characterized in that it reacts with itself, whereas another is characterized in that it undergoes a photoreaction with components of the coating or with components of the matrix material. As the material is exposed to radiation, the absorption is decreased because it is consumed by reacting with itself or with the coating or matrix material. It becomes important to choose a probe constituent that on exposure to radiation does not become non-fluorescent and one such that the absorption of the probe constituent does not change with respect to the degree of cure of the coating or matrix material. Desirably, a probe is selected the emission of which increases or decreases. If the probe is consumed by or reacts with the coating or the matrix material, the absorption of the probe decreases and there occurs a decrease in the emission of the material.

Systems designated types A, B and C are preferred. For a probe reaction with itself in the concentrations used herein, i.e. ppm, the probability of reacting the probe with itself is low. If the concentration of the probe material is increased, the coating or matrix material is perturbed which affects the properties such as aging and cure speed of the material. As the material cures, viscosity increases which increases the difficulty for one molecule of the probe material to reach another. These other kinds of probes just described are not preferred because of the concentration levels present and because the mobility of the probes is decreased as a result of increasing viscosity during cure.

It should be understood that although the preferred embodiment has been described as an article comprising an optical fiber provided with a curable coating system or an array of optical fibers provided with a curable matrix material, that the invention has many other uses. It may be used to monitor the degree of cure of curable materials used to manufacture floor tile, furniture, syringes for medical use, compact audio discs, computer floppy discs, video and audio tapes and glass fiber composites for automobiles and other products.

The invention has been described in terms of adding a probe to a coating or matrix material to provide a material system. It should be understood that the coating or matrix material having a component the emission of light from which is dependent upon the degree of cure may be used.

EXAMPLE 1

One half gram of a solution comprising 0.05 gram 1,3-bispyrenylpropane in 25 ml. N-vinylpyrrolidone was blended with 100 grams of Cabelite 3287-9-11, a UV curable acrylate-based material commercially available from DeSoto, Inc., Des Plaines, Ill. The resulting material system was of Type B. Irradiation of this formulation on release paper with a UV dose of 0.25 Joule/cm$^2$ provided a 0.05 mm film with a 395 nm fluorescence of 73% on a scale of 0 to 100, i.e. 73% of full scale. The instrument 0% reading was set with no sample in the instrument upon excitation at 350 nm. Irradiation of this formulation on release paper with a UV dose of 0.5 J/cm$^2$ provided a 0.05 mm film with a 395 nm fluorescence of 49% upon excitation at 350 nm. Irradiation of this formulation at 1.0 J/cm$^2$ provided a 0.05 mm film with a 395 nm fluorescence of 13% full scale upon excitation at 350 nm.

EXAMPLE 2

One half gram of a solution comprising 0.125 gram 9,10-diphenylanthracene in 25 ml. N-vinylpyrrolidone was blended with 100 grams of Cabelite 3287-9-11, a UV curable material commercially available from DeSoto, Inc., Des Plaines, Ill. The resulting material system relied on changes in the absorption of the UV constituent to effect changes in fluorescence emission of the probe. As such, this is an example of a Type C material system. Irradiation of this formulation on release paper with a UV dose of 0.25 Joule/cm$^2$ provided a 0.05 mm film with 430 nm fluorescence of 57% upon excitation at 380 nm. Irradiation of this formulation on release paper with a UV dose of 1.0 Joule/cm$^2$ provided a 0.05 mm film with a 430 nm fluorescence of 25% upon excitation at 380 nm.

It is to be understood that the above-described arrangements are simply illustrative of the invention. Other arrangements may be devised by those skilled in the art which will embody the principles of the invention and fall within the spirit and scope thereof.

I claim:

1. An optical transmission medium, which comprises:
   an optical fiber transmission medium; and
   a material system which encloses substantially said transmission medium, said material system comprising an ultraviolet light curable material which has been cured and which has an absorbance that depends on the degree of cure of said curable material and a probe comprising a material which emits non-polarized light subsequent to being promoted to an excited electronic state by non-polarized light, the material system being such that its emission of light spans a range dependent upon the degree of cure of said curable material, further, the degree of overlap of the excitation spectra of said probe and said curable material being a function of the behavior of the absorbance of the curable material as the degree of cure changes.

2. The optical transmission medium of claim 1, wherein said probe comprises a fluorescent constituent, the system being such that its fluorescence emission changes as a function of the degree of cure of said curable material.

3. The optical transmission medium of claim 2, wherein the emission increases as the degree of cure of the curable material increases.

4. The optical transmission medium of claim 2, wherein the emission decreases as the degree of cure of the curable material increases.

5. The optical transmission medium of claim 1, wherein the fluorescence of said probe is independent of change in the viscosity of said curable material which is a function of the degree of cure of said curable material.

6. The optical transmission medium of claim 1, wherein said probe comprises a phosphorescent material.

7. The optical transmission medium of claim 1, wherein said material system includes a component which functions as a probe.

8. A method of making a coated optical fiber, said method comprising the steps of:
   moving an optical fiber along a path of travel;
   applying a material system comprising an ultraviolet light curable coating material having an absorbance which depends on the degree of cure of said curable material and a probe to the optical fiber the probe including a fluorescent constituent which is such that it emits light subsequent to being promoted to an excited electronic state and the system being such that its emission of light changes as a function of cure of the curable coating material, further the degree of overlap of the excitation spectrum of the probe being a function of the behavior of the absorbance of the curable material as the degree of cure changes;

curing the coating material;

determining the emission of light of the probe constituent to measure the degree of cure of the curable coating material; and taking up the coated optical fiber.

9. The method of claim 8, wherein said fluorescent probe is such that it is independent of the change in viscosity of said curable material which is a function of the degree of cure of said curable material and the fluorescent emission of said system changes as a function of the degree of cure of the coating material.

10. The method of claim 8, wherein said system comprises at least one coating material and at least one fluorescent probe.

11. The method of claim 8, wherein the said optical fiber comprises an array of optical fibers and said system comprises a matrix material which encloses the array of optical fibers.

12. The method of claim 11, wherein said array is a linear array of optical fibers.

* * * * *